United States Patent
Lee et al.

(10) Patent No.: US 12,018,047 B2
(45) Date of Patent: Jun. 25, 2024

(54) METHOD FOR PRODUCING N-ACETYL DIPEPTIDE AND N-ACETYL AMINO ACID

(71) Applicant: CJ CHEILJEDANG CORPORATION, Seoul (KR)

(72) Inventors: Joo Young Lee, Suwon-si (KR); Chang Suk Lee, Yongin-si (KR); Jin Woo Jeon, Anyang-si (KR); Jun Ok Moon, Yongin-si (KR); Jin Seung Park, Suwon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 448 days.

(21) Appl. No.: 17/282,855

(22) PCT Filed: Nov. 12, 2019

(86) PCT No.: PCT/KR2019/015321
§ 371 (c)(1),
(2) Date: Apr. 5, 2021

(87) PCT Pub. No.: WO2020/101318
PCT Pub. Date: May 22, 2020

(65) Prior Publication Data
US 2021/0347817 A1    Nov. 11, 2021

(30) Foreign Application Priority Data

Nov. 12, 2018 (KR) .................. 10-2018-0138271

(51) Int. Cl.
| | |
|---|---|
| *C07K 1/30* | (2006.01) |
| *B01J 23/02* | (2006.01) |
| *C07C 319/12* | (2006.01) |
| *C07C 319/26* | (2006.01) |
| *C07K 1/02* | (2006.01) |

(52) U.S. Cl.
CPC ............. *C07K 1/306* (2013.01); *B01J 23/02* (2013.01); *C07C 319/12* (2013.01); *C07C 319/26* (2013.01); *C07K 1/02* (2013.01); *C07B 2200/13* (2013.01)

(58) Field of Classification Search
CPC .... B01J 23/02; C07B 2200/13; C07C 319/12; C07C 319/26; C07C 319/20; C07C 323/58; C07K 1/02; C07K 1/306; C07K 5/06026; C07K 5/06043; C07K 5/06052; C07K 5/0606; C07K 5/06069; C07K 5/06078; C07K 5/06086; C07K 5/06095; C07K 5/06104; C07K 5/06113; C07K 5/06147; C07K 5/06156; C07K 5/06165; C07K 1/088; C07K 5/06; C07K 5/06191
See application file for complete search history.

(56) References Cited

U.S. PATENT DOCUMENTS

| | | | |
|---|---|---|---|
| 4,011,263 A | 3/1977 | Wagner et al. | |
| 6,114,163 A * | 9/2000 | Drauz .................. | C07C 227/36 435/106 |
| 2014/0303080 A1 | 10/2014 | Yu et al. | |
| 2016/0207958 A1 | 7/2016 | Matsuyama et al. | |

FOREIGN PATENT DOCUMENTS

| | | |
|---|---|---|
| CN | 101654473 A | 2/2010 |
| CN | 101723772 A | 6/2010 |
| EP | 0876329 B1 | 7/2001 |
| JP | 2007332042 A | 12/2007 |
| KR | 1020160047976 A | 5/2016 |
| SU | 1293171 A1 | 2/1987 |
| WO | 199721667 A1 | 6/1997 |
| WO | 2020101318 A1 | 5/2020 |

OTHER PUBLICATIONS

Sharley et al. (Acetic Acid as a Catalyst for the N-acylation of Amines Using Esters as the Acyl Source, ChemComm., 53, pp. 2020-2023, Published 2017) (Year: 2017).*
CoA (Chemistry of Amides 3 pages, Published 2023) (Year: 2023).*
Extended European Search Report, dated Jul. 8, 2022, issued in EP Patent Application No. 19883713.0, 7 pp.
English Abstract of CN 101723772.
English Abstract of JP 101654473.
English Abstract of JP 2007-332042.
English Abstract of KR 10-2016-0047976.

* cited by examiner

*Primary Examiner* — Yevgeny Valenrod
*Assistant Examiner* — Blaine G Doletski
(74) *Attorney, Agent, or Firm* — CANTOR COLBURN LLP

(57) ABSTRACT

Provided is a method of preparing an N-acetyl dipeptide and an N-acetyl amino acid, the method including producing the N-acetyl dipeptide and the N-acetyl amino acid by reaction of an amino acid with acetic anhydride or acetyl chloride.

12 Claims, 1 Drawing Sheet

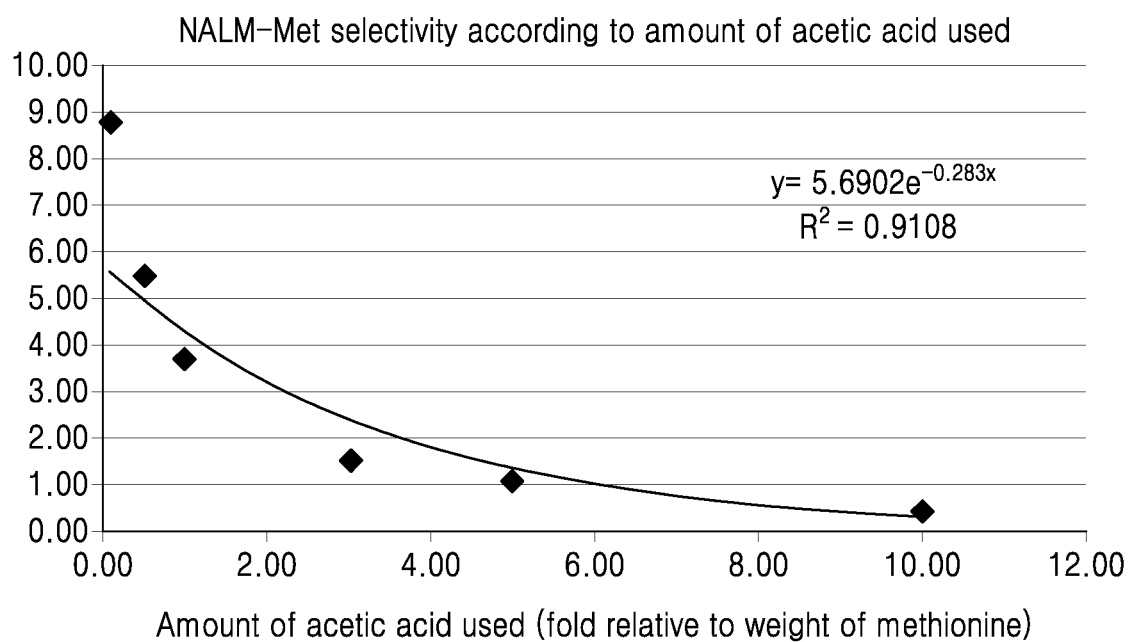

METHOD FOR PRODUCING N-ACETYL DIPEPTIDE AND N-ACETYL AMINO ACID

CROSS-REFERENCE TO RELATED APPLICATIONS

This application is a national stage application of PCT/KR2019/015321, filed on Nov. 12, 2019, which claims priority to and the benefit of KR 10-2018-0138271, filed Nov. 12, 2018 both of which are hereby incorporated by reference in their entirety.

TECHNICAL FIELD

The present disclosure relates to a method of preparing an N-acetyl dipeptide and an N-acetyl amino acid. This work was supported by Korea Institute of Planning and Evaluation for Technology in Food, Agriculture, and Forestry through Agri-Bio industry Technology Development Program funded by Ministry of Agriculture, Food, and Rural Affairs (No. 117030-3).

BACKGROUND ART

A dipeptide, in which two amino acids the same as or different from each other are linked via peptide bonds, is one of the substances used as a major raw material in various fields such as animal nutrition, pharmaceuticals, cosmetics, etc. A dipeptide is used as an antibody drug in the pharmaceutical field, based on its high bioavailability, and is used as a functional cosmetic raw material, based on its cell activation and reactive oxygen species suppressive functions. In the animal nutrition field, amino acids and dipeptides are used as feed additives that serve as a source of protein, and dipeptides exhibit a high absorption rate and stable physical properties for animals. Thus, their use as feeds are of great value. In addition, N-acetyl dipeptide, which is a dipeptide derivative, is digested by a digestive action in the digestive system of animals, and is decomposed into dipeptide and acetic acid. Through this decomposition, N-acetyl dipeptide may display the function of dipeptide, and simultaneously, the additional function of acetic acid used as an energy source in the body.

Existing methods of synthesizing such dipeptides include a liquid dipeptide synthesis method and a method based on N-acetylation reaction of amino acids. The former method requires two or more reactions involving protection and deprotection of functional groups and use of expensive coupling agents. The method based on the N-acetylation reaction of amino acids also proceeds in a two-step reaction followed by a reaction to synthesize an intermediate azlactone, and proceeds at a high temperature of 100° C. or higher. Moreover, in the N-acetylation reaction, N-acetyl amino acids are synthesized from amino acids in a high yield of 90% or more, while dipeptides are synthesized in the yield of less than 10%.

The existing methods have disadvantages of requiring high preparation costs and a long preparation time due to the use of the expensive coupling agents and multiple-step reactions, and since the methods are preparation methods of preparing dipeptides or N-acetyl amino acids as a main substance, it is difficult to prepare dipeptide mixtures with various composition ratios. Accordingly, there is a need to develop a preparation process capable of controlling the composition ratio of dipeptides while reducing product preparation costs and time by simplifying the process of preparing dipeptides into a single step.

PRIOR ART DOCUMENTS

Patent Documents (Patent Document 0001) Korean Patent No. 10-1723649.

DESCRIPTION OF EMBODIMENTS

Technical Problem

An aspect provides a method of preparing an N-acetyl dipeptide and an N-acetyl amino acid.

Solution to Problem

An aspect provides a method of preparing an N-acetyl dipeptide and an N-acetyl amino acid, the method including producing the N-acetyl dipeptide and the N-acetyl amino acid by reaction of an amino acid with acetic anhydride or acetyl chloride.

As used herein, the term "amino acid" may refer to all organic substances including amino groups and carboxyl groups. The amino acid is an important component constituting a protein, and may be represented by the following Formula 1:

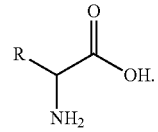

[Formula 1]

In Formula 1, R is an amino acid side chain, and may be hydrogen or a substituent having one or more carbon atoms, but is not limited thereto, and may include all substituents known as the amino acid side chain.

The amino acid may be L-amino acid, for example, alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine.

As used herein, the term "N-acetyl amino acid" may refer to an amino acid in which an acetyl group is bound to a nitrogen atom of an amino group of an amino acid.

As used herein, the term "dipeptide" refers to a polymer in which two amino acids are bound via peptide bonds, and may refer to a polymer in which two amino acids of Formula 1 are bound. The dipeptide may be formed by a dehydration condensation reaction whereby one water molecule is removed from a carboxyl group of a first amino acid and an amino group of a second amino acid to form a peptide bond. The dipeptide may be a molecule in which two identical or different amino acids are bound.

As used herein, the term "N-acetyl dipeptide" is a dipeptide in which an acetyl group is bound to a nitrogen atom of a polymer where two amino acids are bound via a peptide bond, and may be represented by the following Formula 2:

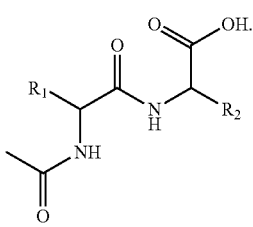

[Formula 2]

In Formula 2, $R_1$ and $R_2$ are amino acid side chains, and may be hydrogen or a substituent having one or more carbon atoms, but are not limited thereto, and may include all substituents known as the amino acid side chain. Further, $R_1$ and $R_2$ may be the same as or different from each other.

The acetic anhydride may be one of carboxylic acid anhydrides, and may be an organic acid anhydride produced by eliminating one molecule of water from two molecules of acetic acid. The acetic anhydride may have a molecular weight of 102.09, a melting point of −73° C., a boiling point of 140.0° C., and a specific gravity of 1.0871 (15° C.), and is also referred to as ethanoic anhydride.

The acetyl chloride is an acyl chloride derived from acetic acid and may be a kind of carboxylic acid chloride. The acetyl chloride has a formula of $CH_3COCl$, and is a colorless liquid, and may have a molecular weight of 78.50, a melting point of −112° C. a boiling point of 51° C., and a specific gravity of 1.104.

In the above method, the N-acetyl dipeptide and the N-acetyl amino acid are reaction products or final products of the reaction, and the method may obtain N-acetyl dipeptide and N-acetyl amino acid through a single reaction.

In producing the N-acetyl dipeptide and the N-acetyl amino acid by reaction of an amino acid with acetic anhydride or acetyl chloride, the reaction may be performed in a solvent. Specifically, the solvent may be an organic acid that maintains a liquid state at room temperature. The organic acid collectively refers to acidic organic compounds. The organic acid may include ascorbic acid, uric acid, carboxylic acid, sulfonic acid, sulfinic acid, phenol, etc. Specifically, the solvent may be, for example, carboxylic acid. The carboxylic acid collectively refers to a compound having a carboxyl group in the molecule. The carboxylic acid is classified into monocarboxylic acid, dicarboxylic acid, tricarboxylic acid, etc., depending on the number of carboxyl groups contained in one molecule, and is also classified into aliphatic carboxylic acid and aromatic carboxyl acid depending on the atomic group bound to the carboxyl group. The carboxylic acid may include formic acid (methanoic acid), acetic acid (ethanoic acid), propionic acid, oxalic acid, malonic acid, succinic acid, palmitic acid, stearic acid, oleic acid, benzoic acid, butyric acid, caproic acid, short-chain fatty acids, salicylic acid, etc. However, it is not limited thereto.

More specifically, the solvent may be, for example, acetic acid. The acetic acid has a formula of $CH_3COOH$, and is called glacial acetic acid, or ethanoic acid. The acetic acid is a colorless liquid with a strong irritating odor, and may have a molecular weight of 60.05, a melting point of 16.6° C., a boiling point of 117.8° C., and a specific gravity of 1.0492.

The solvent may be 0.05 times to 10 times, specifically, 0.05 times to 8 times, 0.05 times to 5 times, 0.05 times to 3 times, 0.05 times to 1 time, 0.05 times to 0.5 times, 0.05 times to 0.1 time, 0.1 time to 10 times, 0.1 time to 8 times, 0.1 time to 5 times, 0.1 time to 3 times, 0.1 time to 1 times, or 0.1 time to 0.5 times the mass of the amino acid. However, it is not limited thereto.

In producing the N-acetyl dipeptide and the N-acetyl amino acid by reaction of an amino acid with acetic anhydride or acetyl chloride, the reaction may be performed in the presence of a catalyst. The catalyst may increase a reaction rate in the reaction or may affect a composition ratio of the reaction products.

The catalyst may be a calcium salt, an ammonium salt, a phosphoric acid, a phosphate, or an alkali salt. The calcium salt may include calcium chloride, calcium acetate, calcium propionate, calcium nitrate, calcium sulfate, calcium carbonate, calcium hydroxide, etc., but is not limited thereto. Specifically, the calcium salt may be calcium chloride or calcium hydroxide, but is not limited thereto. The ammonium salt may include ammonium chloride, ammonium nitrate, ammonium sulfate, ammonium carbonate, etc., but is not limited thereto. The alkali salt is a salt produced by neutralization of a hydroxide of an alkali metal and an acid, and may be also called an alkali metal salt. The alkali metal salt may be sodium chloride or potassium chloride, but is not limited thereto.

A molar ratio of the catalyst may be 0.01 to 0.5 relative to an amino acid to be reacted. Specifically, the molar ratio of the catalyst relative to an amino acid may be 0.01 to 0.4, 0.01 to 0.3, 0.01 to 0.2, 0.01 to 0.1, 0.01 to 0.05, 0.02 to 0.5, 0.02 to 0.4, 0.02 to 0.3, 0.02 to 0.2, 0.02 to 0.1, 0.02 to 0.05, 0.02 to 0.04, 0.03 to 0.5, 0.03 to 0.5, 0.03 to 0.4, 0.03 to 0.3, 0.03 to 0.2, 0.03 to 0.1, 0.03 to 0.05, 0.03 to 0.04, but is limited thereto.

In addition, the catalyst may be used in the number of moles of 1% to 50% relative to the number of moles of an amino acid to be reacted. Specifically, the catalyst may be used in the number of moles of 1% to 40%, 1% to 30%, 1% to 20%, 1% to 10%, 1% to 5%, 2% to 50%, 2% to 40%, 2% to 30%, 2% to 20%, 2% to 10%, 2% to 5%, 2% to 4%, 3% to 50%, 3% to 40%, 3% to 30%, 3% to 20%, 3% to 10%, 3% to 5%, 3% to 4% relative to the number of moles of an amino acid to be reacted, but is not limited thereto.

In producing N-acetyl dipeptide and N-acetyl amino acid by reaction of an amino acid with acetic anhydride or acetyl chloride, the reaction may be performed at 0° C. to 50° C., 5° C. to 40° C., 10° C. to 35° C., specifically at 10° C. to 30° C., and more specifically, at 12° C. to 30° C., 15° C. to 30° C., 17° C. to 30° C., 18° C. to 30° C., 20° C. to 30° C., 22° C. to 30° C., 25° C. to 30° C., 27° C. to 30° C., or 28° C. to 30° C., but is not limited thereto. The reaction may be performed for 3 hours to 12 hours, specifically, for 4 hours to 12 hours, 5 hours to 12 hours, 6 hours to 12 hours, 7 hours to 12 hours, 8 hours to 12 hours, 9 hours to 12 hours, 10 hours to 12 hours, 11 hours to 12 hours, or 12 hours, but is not limited thereto. The reaction may be performed under stirring, but is not limited thereto. The reaction may be performed for an appropriate time until the reaction is terminated to generate N-acetyl dipeptide and N-acetyl amino acid.

The method of preparing N-acetyl dipeptide and N-acetyl amino acid may further include, after producing the N-acetyl dipeptide and N-acetyl amino acid, obtaining a liquid concentrate by concentrating the reaction solution containing the reaction product obtained in the above reaction or obtaining crystals by crystallizing the reaction solution containing the reaction product or the liquid concentrate.

The obtaining of the liquid concentrate may be concentrating the reaction solution containing the reaction product at 50° C. to 90° C., specifically, at 50° C. to 85° C., 50° C. to 80° C., 50° C. to 75° C., 55° C. to 90° C., 55° C. to 85°

C., 55° C. to 80° C., 55° C. to 75° C., 60° C. to 90° C., 60° C. to 85° C., 60° C. to 80° C., 60° C. to 75° C., 65° C. to 90° C., 65° C. to 85° C., 65° C. to 80° C., or 65° C. to 75° C. under reduced pressure, but is not limited thereto. The reduced pressure may be 10 torr to 50 torr, specifically, 10 torr, 15 torr, 20 torr, 25 torr, 30 torr, 35 torr, 40 torr, 45 torr, or 50 torr or less, but is not limited thereto.

A common technique known in the art may be applied to the obtaining of the crystals. For example, the obtaining of the crystals may be performed by diluting the reaction solution containing the reaction product or the liquid concentrate obtained by concentrating the reaction solution using an aqueous sodium chloride solution, or a mixed solution of ethyl acetate and sodium chloride, and then stirring the solution at a reduced temperature. The process of reducing the temperature may be, for example, reducing the temperature to 5° C. to 40° C., 5° C. to 35° C., 5° C. to 30° C., 5° C. to 25° C., 5° C. to 20° C., or 5° C. to 15° C. The crystals produced in obtaining the crystals may be separated according to a common technique known in the art, for example, may be separated through vacuum filtration.

In the above method, a molar ratio of N-acetyl dipeptide to N-acetyl amino acid in the reaction solution containing the reaction product, i.e., selectivity may be 0.5 or more.

As used herein, the term "selectivity" may refer to a molar ratio of N-acetyl dipeptide to N-acetyl amino acid, and may be a value calculated by the following Equation 1:

Selectivity=Mol % of NALM-Met/Mol % of NALM. [Equation 1]

The molar ratio of N-acetyl dipeptide to N-acetyl amino acid may be 0.5 to 9.0, specifically, 1.0 to 9.0, 2.0 to 9.0, 2.5 to 9.0, 3.0 to 9.0, 3.5 to 9.0, 4.0 to 9.0, 5.0 to 9.0, 6.0 to 9.0, 0.5 to 0.7, 0.7 to 0.8, 0.8 to 0.9, 0.9 to 1.0, 1.0 to 1.5, 1.5 to 2.0, 2.0 to 2.5, 2.5 to 3.0, 3.0 to 3.5, 3.5 to 4.0, 4.0 to 4.5, 4.5 to 5.0, 5.0 to 5.5, 5.5 to 6.0, 6.0 to 6.5, 6.5 to 7.0, 7.0 to 7.5, 7.5 to 8.0, 8.0 to 8.5, or 8.5 to 9.0, but is not limited thereto.

The selectivity of N-acetyl dipeptide with respect to N-acetyl amino acid may vary by controlling a molar ratio of the used catalyst to amino acids, a mass ratio of the used solvent to amino acids, a reaction temperature, etc. in producing N-acetyl dipeptide and N-acetyl amino acid by reaction of the amino acid with acetic anhydride or acetyl chloride.

In a specific embodiment, as the mass of acetic acid used as a solvent increases, the selectivity of N-acetyl dipeptide with respect to N-acetyl amino acid may decrease. The decrease in the selectivity of N-acetyl dipeptide according to the increase in the mass of acetic acid has an exponential function relationship of $0<a<1$, as in the following Equation 2, when the multiple of the mass of acetic acid with respect to the mass of amino acid is x and the selectivity of N-acetyl dipeptide is y. As the x value increases, the y value may decrease by $a^x$:

$y=a^x$. [Equation 2]

In producing the N-acetyl dipeptide and the N-acetyl amino acid by reaction of an amino acid with acetic anhydride or acetyl chloride, when a value varying depending on the type of the amino acid to be reacted and the solvent to be used is obtained, N-acetyl dipeptide of the desired selectivity may be prepared by controlling the mass of the solvent in the reaction, and the mass of the solvent may be controlled according to the required selectivity of N-acetyl dipeptide.

Advantageous Effects of Disclosure

A method of preparing an N-acetyl dipeptide and an N-acetyl amino acid by reacting an amino acid with acetic anhydride or acetyl chloride according to an aspect may prepare the N-acetyl dipeptide and the N-acetyl amino acid with higher economic efficiency by a single reaction. Further, when the preparation method is used, selectivity of N-acetyl dipeptide with respect to N-acetyl amino acid may be controlled.

BRIEF DESCRIPTION OF DRAWINGS

FIG. 1 is a graph showing changes in selectivity of N-acetyl dipeptide with respect to N-acetyl amino acid according to the amount of acetic acid.

MODE OF DISCLOSURE

Hereinafter, the present disclosure will be described in more detail with reference to exemplary embodiments. However, these exemplary embodiments are only for illustrating the present disclosure, and the scope of the present disclosure is not limited to these exemplary embodiments.

Example 1. Selectivity of N-Acetyl Methionine Dipeptide (NALM-Met) According to Kind of Catalyst To compare selectivity of N-acetyl methionine dipeptide (hereinafter, 'NALM-Met') and N-acetyl methionine (hereinafter, 'NALM') according to the kind of catalyst, methionine (0.67 mol), acetic anhydride (0.70 mol), and acetic acid (1.83 mol) were mixed, and 0.025 mol of one of $Ca(OH)_2$, $CaCl_2$, $Cu(OH)_2CO_3$, $CuSO_4$, $NH_4Cl$, $CH_3CO_2Na$, $H_3PO_4$, and NaCl as a salt catalyst was added thereto, followed by stirring at room temperature for 4 hours. As a control group, an experimental group, in which no salt was added under the same conditions, was used. When completion of the reaction was confirmed by TLC, the sample was taken and diluted 500-fold, and then concentrations thereof were examined by HPLC analysis, and selectivity of N-acetyl methionine dipeptide (NALM-Met) was calculated according to the following equation, and results are shown in Table 1.

Selectivity=Mol % of NALM-Met/Mol % of NALM. [Equation 1]

TABLE 1

| Kind of catalyst | Composition of N-acetyl dipeptide and N-acetyl amino acid in reaction solution | | |
|---|---|---|---|
| | NALM-Met (mol %) | NALM (mol %) | Selectivity |
| Control group | 38.55 | 56.44 | 0.68 |
| $Ca(OH)_2$ | 70.99 | 19.33 | 3.67 |
| $CaCl_2$ | 65.66 | 19.4 | 3.38 |
| $Cu(OH)_2CO_3$ | 15.87 | 67.99 | 0.23 |
| $CuSO_4$ | 19.33 | 66.3 | 0.29 |
| $NH_4Cl$ | 35.12 | 46.86 | 0.75 |
| $CH_3CO_2Na$ | 41.28 | 44.02 | 0.94 |
| $H_3PO_4$ | 39.86 | 50.12 | 0.80 |
| NaCl | 37.45 | 58.54 | 0.64 |

As an experimental result, when a calcium salt of $Ca(OH)_2$ or $CaCl_2$ among the catalysts of Table 1 was added as the catalyst, selectivity was increased about 5.4 times or about 5.0 times, as compared with that of the control group. When an additive in the form of a copper salt of $CuSO_4$ or $Cu(OH)_2CO_3$ was added, NALM-Met selectivity was decreased, as compared with the control group. Therefore, it was confirmed that use of the catalyst in the form of calcium salt ($Ca^{2+}$) is suitable for increasing NALM-Met selectivity.

Example 2. Selectivity of NALM-Met According to Amount of $Ca(OH)_2$

To compare selectivity according to the amount of $Ca(OH)_2$ which is the most excellent in improving the selectivity of N-acetyl methionine dipeptide as compared with the control group in Example 1, methionine (0.67 mol), acetic anhydride (0.70 mol), and acetic acid (1.83 mol) were mixed, and $Ca(OH)_2$ was injected in an amount of 0%, 2.5%, 3.75%, 5%, 10%, 20%, or 40% relative to the number of moles of methionine, followed by stirring at room temperature for 4 hours. As a control group, an experimental group, in which $Ca(OH)_2$ was not used, was used. When completion of the reaction was confirmed by TLC, the sample was taken and diluted 500-fold, and then concentrations thereof were examined by HPLC analysis, and selectivity was calculated according to Equation 1, and results are shown in Table 2.

TABLE 2

| $Ca(OH)_2$ injection % | Composition of N-acetyl dipeptide and N-acetyl amino acid in reaction solution | | |
|---|---|---|---|
| | NALM-Met (mol %) | NALM (mol %) | Selectivity |
| 0.00% (Control group) | 38.55 | 56.44 | 0.68 |
| 2.50% | 74.73 | 19.17 | 3.90 |
| 3.75% | 74.86 | 18.67 | 4.01 |
| 5.00% | 68.28 | 18.58 | 3.67 |
| 10.00% | 72.18 | 23.18 | 3.11 |
| 20.00% | 66.93 | 27.30 | 2.45 |
| 40.00% | 62.84 | 34.10 | 1.84 |

As an experimental result, in all experimental groups in which $Ca(OH)_2$ was injected, NALM-Met selectivity was improved, as compared with the control group, and the most excellent effect was observed when 3.75% thereof was injected.

Example 3. Selectivity of NALM-Met According to Amount of Acetic Acid

To compare selectivity of N-acetyl methionine dipeptide according to the amount of acetic acid which is a solvent, methionine (0.67 mol), acetic anhydride (0.70 mol), and $Ca(OH)_2$ (0.025 mol) were mixed, and acetic acid was injected in an amount of 0.1, 0.5, 1.0, 3.0, 5.0, or 10.0-fold relative to the mass of methionine, followed by stirring at room temperature for 4 hours. When completion of the reaction was confirmed by TLC, the sample was taken and diluted 500-fold, and then concentrations thereof were examined by HPLC analysis, and selectivity was calculated according to Equation 1, and results are shown in Table 3 and FIG. 1.

TABLE 3

| Injection fold of acetic acid | Composition of N-acetyl dipeptide and N-acetyl amino acid in reaction solution | | |
|---|---|---|---|
| | NALM-Met (mol %) | NALM (mol %) | Selectivity |
| 0.1-fold | 76.12 | 8.65 | 8.80 |
| 0.5-fold | 73.10 | 13.34 | 5.48 |
| 1.0-fold | 71.44 | 19.36 | 3.69 |

TABLE 3-continued

| Injection fold of acetic acid | Composition of N-acetyl dipeptide and N-acetyl amino acid in reaction solution | | |
|---|---|---|---|
| | NALM-Met (mol %) | NALM (mol %) | Selectivity |
| 3.0-fold | 57.69 | 37.02 | 1.56 |
| 5.0-fold | 49.45 | 44.89 | 1.10 |
| 10.0-fold | 27.54 | 63.98 | 0.43 |

As an experimental result, the amount of acetic acid and the selectivity of NALM-Met were found to have a significant exponential function relationship. This result indicates that the composition ratio of NALM-Met and NALM in the reaction solution may be appropriately controlled according to the purpose by controlling the amount of acetic acid.

Example 4. Selectivity of NALM-Met According to Reaction Temperature

To compare selectivity of N-acetyl methionine dipeptide according to the reaction temperature, methionine (0.67 mol), acetic anhydride (0.70 mol), acetic acid (1.83 mol), and $Ca(OH)_2$ (0.025 mol) were mixed, followed by stirring at 10° C. or room temperature (25° C.). When completion of the reaction was confirmed by TLC, the reaction was completed at 10° C. 12 hours later, and completed at room temperature 4 hours later. When the reaction was completed, the sample was taken and diluted 500-fold, and then concentrations thereof were examined by HPLC analysis, and selectivity was calculated according to Equation 1, and results are shown in Table 4.

TABLE 4

| Reaction temperature | Composition of N-acetyl dipeptide and N-acetyl amino acid in reaction solution | | |
|---|---|---|---|
| | NALM-Met (mol %) | NALM (mol %) | Selectivity |
| 10° C. | 74.44 | 14.18 | 5.25 |
| 25° C. | 65.91 | 19.91 | 3.31 |

As an experimental result, the increased reaction temperature increased the conversion ratio into NALM and decreased NALM-Met selectivity. At room temperature, 4 hours were required until the reaction was completed. However, at 10° C., a total of 12 hours were required and thus the reaction time was greatly increased. The conditions for prolonging the reaction time or cooling the reaction temperature may reduce efficiency and economic efficiency of the process, and thus the method of controlling the amount of solvent is more suitable than the method of controlling the reaction temperature, in order to increase the selectivity of N-acetyl methionine dipeptide.

Example 5. Preparation of N-Acetyl Methionine Dipeptide (NALM-Met)

To obtain N-acetyl methionine dipeptide (NALM-Met) according to the results of increasing selectivity in Examples 1 to 4, methionine (0.67 mol), acetic anhydride (0.70 mol), acetic acid (1.83 mol), and $Ca(OH)_2$ (0.025 mol) were mixed, followed by stirring at room temperature for 4 hours. When completion of the reaction was confirmed by TLC, the reaction solution was concentrated at 70° C. and at a reduced pressure of 25 torr. Distilled water (300 g) and NaCl (0.67 mol) were added to the liquid concentrate, and cooled to 7° C., and crystallized by stirring for 12 hours. The resulting crystals were filtered under reduced pressure to obtain N-acetyl methionine dipeptide which is a target reaction product, and its yield was 80.5% and the content of NALM-Met was 88.6 w/w % and the content of NALM was 2.76 w/w %, relative to the final solid crystals.

Example 6. Preparation of N-Acetyl Phenylalanine Dipeptide (NALP-Phe)

In N-acetyl phenylalanine dipeptide (NALP-Phe), the abbreviation NALP represents N-acetyl-phenylalanine, and the abbreviation Phe represents phenylalanine. Phenyl alanine (0.67 mol), acetic anhydride (0.70 mol), acetic acid (2.74 mol), and Ca(OH)$_2$ (0.025 mol) were mixed, followed by stirring at room temperature for 6 hours. When completion of the reaction was confirmed by TLC, the reaction solution was concentrated at 70° C. and at a reduced pressure of 25 torr. Distilled water (300 g) and NaCl (0.67 mol) were added to the liquid concentrate, and cooled to 7° C., and crystallized by stirring for 12 hours. The resulting crystals were filtered under reduced pressure to obtain N-acetyl phenylalanine dipeptide (NALP-Phe) which is a target reaction product, and its yield was 82.61% and the content of NALP-Phe was 87.62 w/w % and the content of NALP was 3.37 w/w %, relative to the final solid crystals.

Example 7. Preparation of N-Acetyl Valine Dipeptide (NALV-Val)

In N-acetyl valine dipeptide (NALV-Val), the abbreviation NALV represents N-acetyl-valine, and the abbreviation Val represents valine. Valine (0.67 mol), acetic anhydride (0.70 mol), acetic acid (1.83 mol), and Ca(OH)$_2$ (0.025 mol) were mixed, followed by stirring at room temperature for 2 hours. When completion of the reaction was confirmed by TLC, the reaction solution was concentrated at 70° C. and at a reduced pressure of 25 torr. Ethyl acetate (300 g) and NaCl (0.67 mol) were added to the liquid concentrate, and cooled to 7° C., and crystallized by stirring for 12 hours. The resulting crystals were filtered under reduced pressure to obtain N-acetyl valine dipeptide (NALV-Val) which is a target reaction product, and its yield was 61.25% and the content of NALV-Val was 90.62 w/w % and the content of NALV was 1.31 w/w %, relative to the final solid crystals.

Example 8. Selectivity According to Use of Acetic Anhydride or Acetyl Chloride To compare selectivity of N-acetyl methionine dipeptide according to reactants, methionine (0.67 mol), Ca(OH)$_2$ (0.025 mol), and acetic acid (1.83 mol) were mixed, and acetic anhydride (0.70 mol) or acetyl chloride (0.70 mol) was added thereto, followed by stirring at room temperature for 4 hours. When completion of the reaction was confirmed by TLC, the sample was taken and diluted 500-fold, and then concentrations thereof were examined by HPLC analysis, and selectivity was calculated according to Equation 1, and results are shown in Table 5.

TABLE 5

| Reactant | Composition of N-acetyl dipeptide and N-acetyl amino acid in reaction solution | | |
|---|---|---|---|
| | NALM-Met (mol %) | NALM (mol %) | Selectivity |
| Acetic anhydride | 74.73 | 19.17 | 3.90 |
| Acetyl chloride | 59.68 | 23.95 | 2.48 |

As an experimental result, it was confirmed that when acetyl chloride was used as a reactant with amino acids, selectivity of NALM-Met was higher than that of NALM.

The invention claimed is:

1. A method of preparing an N-acetyl dipeptide and an N-acetyl amino acid, the method comprising producing the N-acetyl dipeptide and the N-acetyl amino acid by reaction of an amino acid with acetic anhydride or acetyl chloride, wherein the reaction is performed in the presence of a catalyst, wherein the catalyst is calcium chloride or calcium hydroxide.

2. The method of claim 1, wherein the reaction is performed in an organic acid solvent.

3. The method of claim 2, wherein the solvent is carboxylic acid.

4. The method of claim 2, wherein the solvent is acetic acid.

5. The method of claim 1, wherein the amino acid is alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine.

6. A method of preparing an N-acetyl dipeptide and an N-acetyl amino acid, the method comprising producing the N-acetyl dipeptide and the N-acetyl amino acid by reaction of an amino acid with acetic anhydride or acetyl chloride, wherein the reaction is performed in the presence of a catalyst, wherein a molar ratio of the catalyst to the amino acid is 0.01 to 0.4.

7. The method of claim 2, wherein the solvent is 0.1 time to 5 times the mass of the amino acid.

8. A method of preparing an N-acetyl dipeptide and an N-acetyl amino acid, the method comprising producing the N-acetyl dipeptide and the N-acetyl amino acid by reaction of an amino acid with acetic anhydride or acetyl chloride, wherein the reaction is performed at 10° C. to 30° C.

9. A method of preparing an N-acetyl dipeptide and an N-acetyl amino acid, the method comprising producing the N-acetyl dipeptide and the N-acetyl amino acid by reaction of an amino acid with acetic anhydride or acetyl chloride, wherein the reaction is performed for 3 hours to 12 hours.

10. The method of claim 1, further comprising, after producing the N-acetyl dipeptide and N-acetyl amino acid, obtaining a liquid concentrate by concentrating the reaction solution comprising the reaction product obtained in the above reaction or obtaining crystals by crystallizing the reaction solution comprising the reaction product or the liquid concentrate.

11. A method of preparing an N-acetyl dipeptide and an N-acetyl amino acid, the method comprising producing the N-acetyl dipeptide and the N-acetyl amino acid by reaction of an amino acid with acetic anhydride or acetyl chloride, wherein a molar ratio of the N-acetyl dipeptide to the N-acetyl amino acid is 0.5 or more.

12. A method of preparing an N-acetyl dipeptide and an N-acetyl amino acid, the method comprising producing the N-acetyl dipeptide and the N-acetyl amino acid by reaction of an amino acid with acetic anhydride or acetyl chloride, wherein a molar ratio of the N-acetyl dipeptide to the N-acetyl amino acid is 0.5 to 9.0.

\* \* \* \* \*